| United States Patent [19]
Maren

[11] Patent Number: 4,746,745
[45] Date of Patent: May 24, 1988

[54] 1,3,4-THIADIAZOLINE-5-SULFONAMIDES

[76] Inventor: Thomas H. Maren, University of Florida, College of Medicine, Dept. of Pharmacology & Therapeutics, Gainesville, Fla. 32610

[21] Appl. No.: 845,579

[22] Filed: Jun. 19, 1986

Related U.S. Application Data

[60] Division of Ser. No. 729,907, May 3, 1985, Pat. No. 4,619,939, which is a continuation of Ser. No. 442,672, Nov. 18, 1982, abandoned, which is a continuation-in-part of Ser. No. 319,093, May 29, 1981, abandoned, which is a continuation-in-part of Ser. No. 167,220, Jul. 9, 1980, abandoned.

[51] Int. Cl.$^4$ ................. C07D 285/12; C07D 285/14
[52] U.S. Cl. ..................................................... 548/139
[58] Field of Search ......................... 514/363; 548/139

[56] References Cited

U.S. PATENT DOCUMENTS 2,783,240  2/1957  Vaughan et al. .................. 424/270
3,323,999  6/1967  Nechay et al. .................... 424/270
4,386,098  5/1983  Woltersdorf et al. ............. 424/270
4,438,123  3/1984  Smith ................................ 514/363

OTHER PUBLICATIONS

Am. J. Vet. Res., vol. 40(3), 334–344 (1979)–Gelatt et al.
AMA. Drug Evaluations–2nd ed. (1973)–pp. 675, 684–685, publ. Sci. Group Inc., Anton, Mass.
Chem. Abst. 55:10472(a) (1961)–Young.
Chem. Abst. 99:47544(q) (1983)–Maren et al.
Chem. Abst. 102:56099(f) (1985)–Bar–Ilan.
Chem. Abst. 102:214528(b) (1985)–Conroy et al.
Chem. Abst. 104:122527(p) (1986)–Jankowska et al.

*Primary Examiner*—Douglas W. Robinson
*Attorney, Agent, or Firm*—Dennis P. Clarke

[57] ABSTRACT

Process and composition for reducing intraocular pressure and reducing aqueous humor formation by applying topically to the cornea an effective amount of an aqueous solution of a caronic anhydrase inhibitor comprising a sulfonamide having the following properties:
  a. sufficiently soluble in water to form at least a 3 mM solution at pH 8.2 or a pKa of not greater than 7.3;
  b. ether partition coefficient of at least 1.0;
  c. chloroform partition coefficient of at least 0.01;
  d. dissociation constant against carbonic anhydrase of not more than $3 \times 10^{-8}$ molar;
  e. first order rate constant for penetration of the sulfonamide through a living rabbit cornea of at least 0.005 hr$^{-1}$;
  f. not injurious to the cornea; and
  g. stable in aqueous solution and in contact with the cornea.

2 Claims, 3 Drawing Sheets

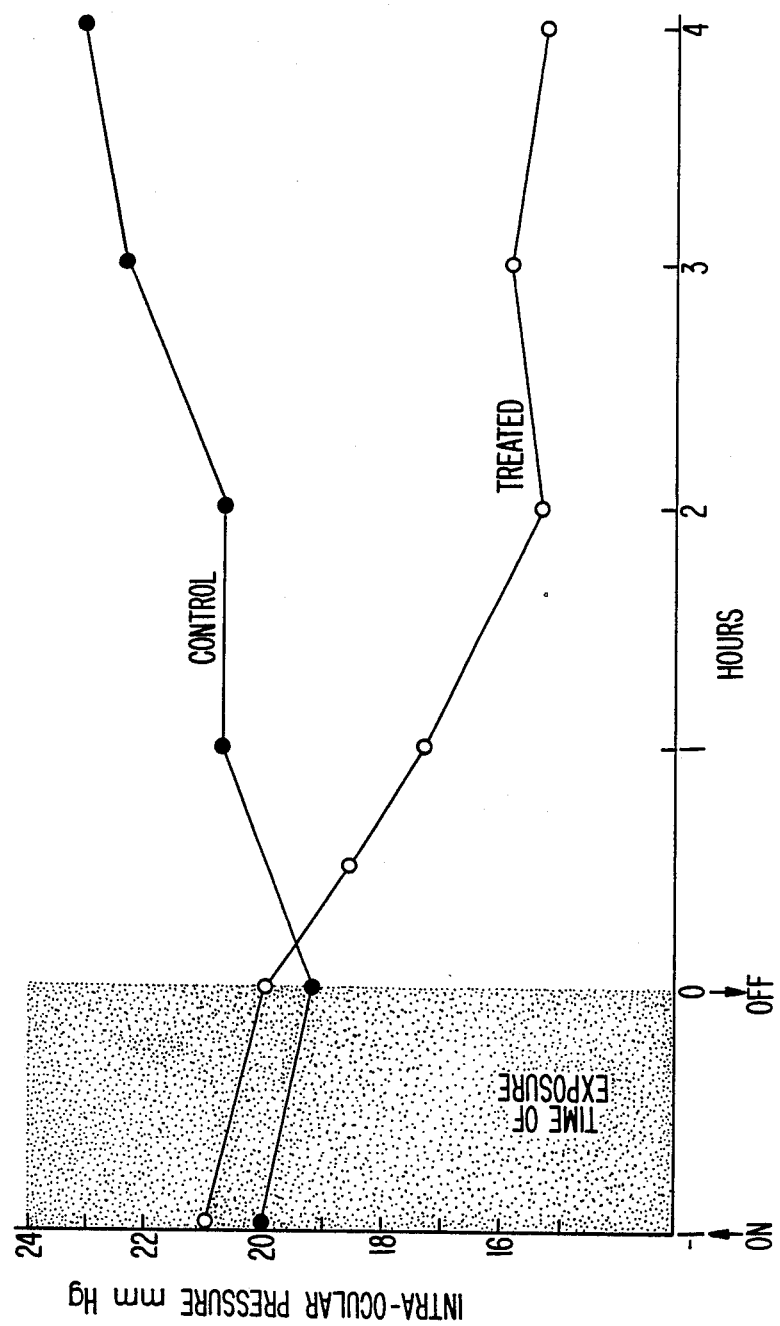

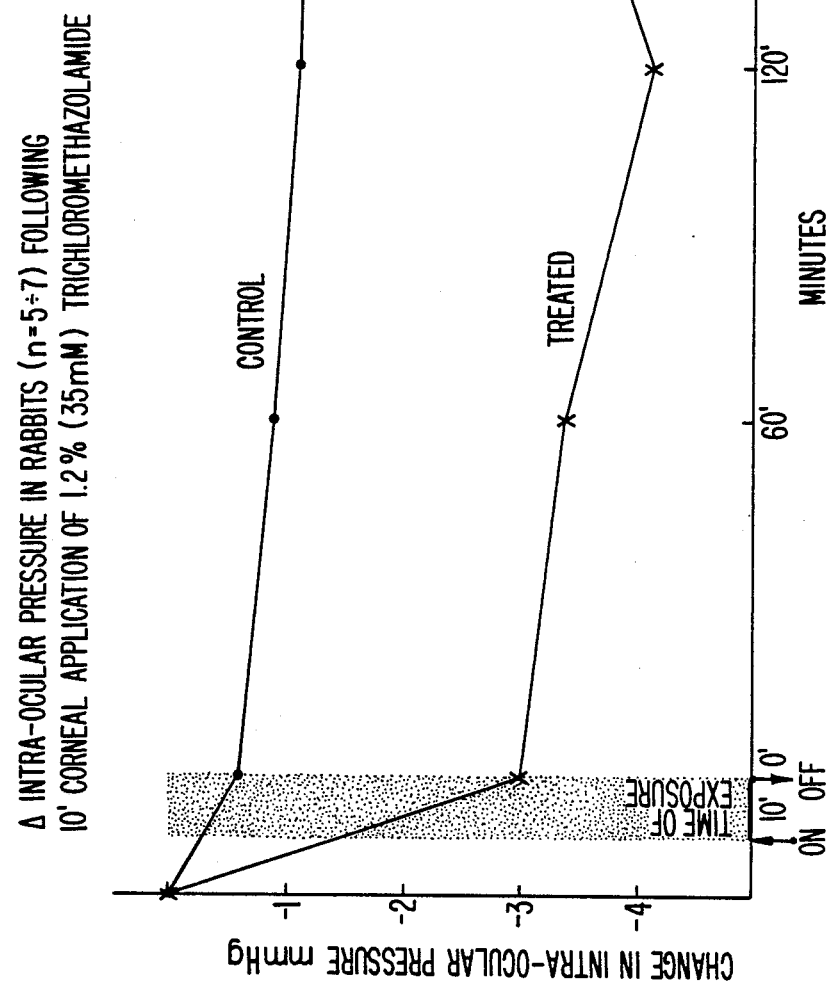

1,3,4-THIADIAZOLINE-5-SULFONAMIDES

RELATED U.S. PATENT APPLICATION DATA

This application is a divisional of Ser. No. 729,907, filed May 3, 1985, now U.S. Pat. No. 4,619,939, which is a continuation of Ser. No. 442,672, filed Nov. 18, 1982, now abandoned, which is a continutation-in-part of Ser. No. 319,093, filed May 29, 1981, now abandoned, which is a continuation-in-part of Ser. No. 167,220, filed July 9, 1980, now abandoned.

TECHNICAL FIELD

This invention is directed to a process and composition for reducing intraocular pressure and reducing aqueous humor formation by applying topically to the cornea an effective amount of an aqueous solution of a carbonic anhydrase inhibitor.

BACKGROUND OF THE INVENTION

Glucaoma is well known as a condition in which the internal pressure in the eye increases to the extent that it causes damage to the optic nerve and may eventually cause blindess. This condition is primarily caused by the failure of aqueous humor to properly drain from the eye, resulting in a high internal or intraocular pressure. It has been recognized that the formation of aqueous humor is in part the result of the activity of the enzyme carbonic anhydrase which is employed by the human body to reversibly catalyze the hydration of carbon dioxide. Compounds, principally heterocyclic sulfonamides, are known which inhibit the activity of carbonic anhydrase and thus control the production of aqueous humor and the intraocular pressure resulting therefrom. [Havener, Ocular Pharmacology, 4th Ed. (1978, C. V. Moseby); Maren, Investigative Ophthalmology, Vol. 13, pp. 479–484 (1974); Becker, Am. J. of Ophthalmology, Vol. 39, p. 177 (1955)].

It is necessary to administer these materials parenterally in order to achieve intraocular pressure reduction. Parenteral administration requires relatively large dosages and very often results in the patient experiencing fatigue, depression, anorexia, numbness and tingling sensations.

It has now been discovered that certain carbonic anhydrase inhibitors can be administered topically, i.e., applied directly to the cornea, and that these compounds will penetrate the cornea and be immediately effective in inhibiting the activity of carbonic anhydrase and decreasing intraocular pressure and aqueous humor flow resulting from this activity.

The topical or local applicability of intraocular pressure depressants offers several major advantages over drugs requiring parenteral administration. Topical applicability avoids the unpleasant side effects described above which result from systemic applications of carbonic anhydrase inhibitors. In addition, topical application enables a more rapid, localized concentration of the drug at the situs requiring the drug's action.

BRIEF SUMMARY OF THE INVENTION

This invention provides a method and composition particularly adapted for reducing intraocular pressure and reducing aqueous humor formation. It has been discovered that the topical application to the cornea of certain anhydrase inhibitors effects a reduction of aqueous humor formation and intraocular pressure. These carbonic anhydrase inhibitors comprise pharmaceutically acceptable sulfonamides having the following properties:

a. sufficiently soluble in water to form at least a 3 mM (or approximately 0.1%, by weight) solution at pH 8.2 or pKa of 7.3 or less;
b. ether partition coefficient of at least 1.0 at pH 7.2;
c. chloroform partition coefficient of at least 0.01 at pH 7.2;
d. dissociation constant against carbonic anhydrase of not more than $3 \times 10^{-8}$ molar;
e. first order rate constant for penetration of said sulfonamide through a living rabbit cornea of at least 0.005 $hr^{-1}$;
f. not injurious to the cornea; and
g. stable in solution and in contact with the cornea.

DETAILED DESCRIPTION OF THE INVENTION

Figure 1:
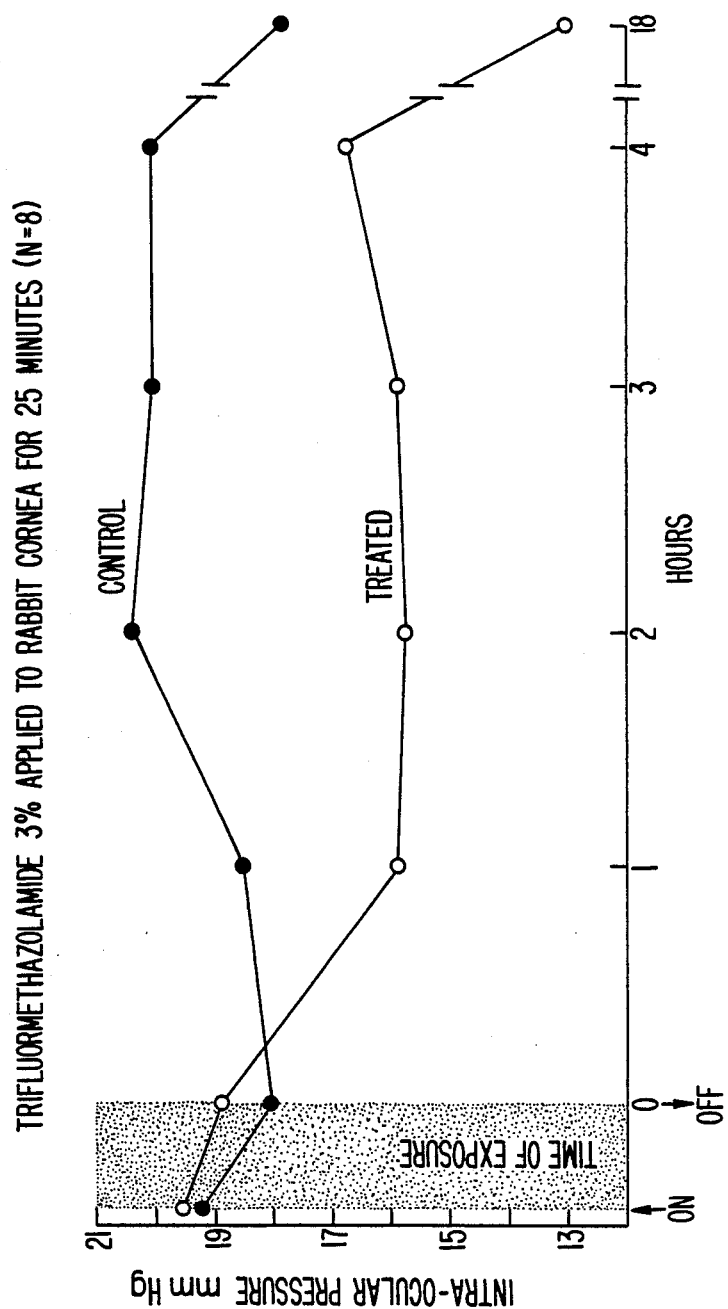

In accordance with the invention it has been found that certain carbonic anhydrase inhibitors can be safely and advantageously applied directly to the cornea in the form of drops of aqueous solution. These inhibitors must have certain properties in order to effectively function in this fashion. First, the inhibitor in its aid form ust have a pKa which is not greater than 7.3, or the inhibitor in the acid form must be sufficiently soluble in water to produce at least a 3 mM (or approximately 0.1%, by weight) solution at pH 8.2. This property is important in that it permits the compound to be used in an at least 3 mM aqueous solution at a pH below 8.2 and therefore can be applied to the eye at a relatively neutral pH. The pKa may be measured by titrating the compound with NaOH and finding the point at which half of the compound is neutralized. The pH at this point is the pKa.

Another necessary property of these compounds is that they must possess an ether partition coefficient of at least 1.0. This property in conjunction with the chloroform coefficient is a measure of the lipid solubility of this compound. This is a critical feature since the compound must be readily absorbed by the lipid materials in the eye and be available for intimate contact with carbonic anhydrase so as to control its activity. This property is measured by preparing an aqueous solution of the compound at pH 7.2 and shaking the solution with an equal volume of ether until equilibrium is achieved in the system. An ether layer and an aqueous layer are formed, separated, and each analyzed for its content of the compound. The coefficient is the ratio of the amount of the compound in the ether layer to the amount of the compound in the aqueous layer. See, e.g., Maren, J. Pharm. Expt. Therap. Vol. 130, p. 26, (1960) for the method of analysis for the compound in each layer.

Another critical property necessary in the inhibitors employed in this invention is the chloroform partition coefficient which must be at least 0.01. This property also relates to the lipid solubility of the compound employed and it is measured as described above with respect to ether. The procedure is the same as that described above except that chloroform is employed in place of ether.

Another necessary property in the inhibitors employed in this invention is that they must have a disassociation constant against carbonic anhydrase of not more than $3 \times 10^{-8}$ molar. This property denotes that the compound has a high activity against carbonic anhydrase in the ciliary process of the eye which is, at least in part, responsible for the secretion of aqueous humor. The dissociation constant is the concentration of the compound that will inhibit one-half of the carbonic anhydrase in a test system wherein the conditions are so arranged that the compound is present in excess of the carbonic anydrase. The test system is described in Maren, supra, and in a subsequent article by Maren in the same volume at page 389.

Still another critical property of the inhibitor compounds employed in this invention is that the compound must have a first order rate constant for penetration of the compound through a living rabbit cornea of at least $0.005\ hr^{-1}$. This property is important in that it sets a standard for a speed in which the inhibitor will pass through the cornea to the interior of the eye and be available to inhibit the activity of carbonic anhydrase in that location. This is measured by placing a solution of the compound (about 0.5 ml) on the cornea of the living, lightly anesthetized rabbit. The lids are held by light hemostats in such a way as to create a well to hold the solution so that a steady state concentration is achieved. At timed intervals, samples are withdrawn from the anterior chamber of the rabbit and the fluid analyzed for the concentration of drug. The analyses are done by the method of Maren, supra. The data are treated to yield the first order rate constants which are cited herein.

Still another critical property of the compounds employed in this invention is that they be pharmaceutically acceptable and not be injurious to the cornea being treated.

The final property which is necessary for a compound used in this invention is that it be stable against decomposition in solution and in contact with the cornea. This property may be tested by dissolving the compound in aqueous solution and in solution containing corneal tissue to determine whether the compound has remained stable or has decomposed into other materials.

None of the carbonic anhydrase inhibitors previously employed by parenteral administration is useful in the process of this invention because they do not meet all of the criteria mentioned above and therefore cannot be used topically. Perhaps the best known inhibitor in the prior art is acetazolamide (2-acetylamino-1,3,4-thiadiazole-5-sulfonamide) which cannot be made into a water solution below pH 8 at concentrations sufficiently high to enable its use effectively as a topically applied agent. Moreover, the pKa of acetazolamide is 7.4; the ether partition coefficient is 0.14 and the chloroform coefficient is 0.001. This material has been tried and found to be completely unsuitable in lowering intraocular pressure by topical adminstration. [Foss, Am. J. Ophthalmology, Vol. 39, p. 336 (1955)]. Methazolamide (2-acetylimino-3-methyl-$\Delta^2$-1,3,4-thiadiazoline-5-solufonamide) is another known carbonic anhydrase inhibitor but it is unsuitable in the process of this invention. This compound has a pKa of 7.4 and cannot be made into a neutral solution with a sufficiently high concentration to enable topical application. In a series of tests employing methazolamide topically the intraocular pressure was not reduced except to a very slight extent in one of the series of tests. Still another prior art inhibitor is ethoxzolamide (6-ethoxy-benzothiazole-2-sulfonamide) having properties somewhat similar to those of methazolamide. This material has a pKa of 8.1 and cannot be made into an aqueous solution at a concentration above about 0.004%. This drug is ineffective in topically treating the eye to reduce intraocular pressure.

A compound which is useful in the process of this invention is 2-trifluoroacetylimino-3-methyl-$\Delta^2$-1,3,4-thiadiazoline-5-sulfonamide, its common name being trifluoromethazolamide. This compound meets all of the qualifications as set forth for the process of this invention. This compound has a pKa of 6.6; an ether partition coefficient of 6.0; a chloroform partition coefficient of 0.3; a dissociation constant of $3 \times 10^{-8}$ molar; an in vivo rabbit cornea penetration rate constant of $0.014\ hr^{-1}$; it does not injure or cloud the cornea in a 2–5% solution; and is stable in solution for two hours.

Another compound useful in this invention is 2-trichloroacetylimino-3-methyl-$\Delta^2$-1,3,4-thiadiazoline-5-sulfonamide, its common name being trichloromethazolamide. It has a pKa of 7.0; an ether partition coefficient of 56, a chloroform partition coefficient of 4; a dissociation constant of $2 \times 10^{-8}$ molar; an in vivo rabbit cornea penetration rate constant of $0.063\ hr^{-1}$; it does not injure or cloud the cornea in 2–5% solution; and it is stable in solution for at least six hours.

An additional compound satisfying the above criteria is 2-orthochlorophenylthiadiazole-5-sulfonamide. The compound has a pKa of 7.3, an ether partition coefficient of 25, a chloroform partition coefficient of 10, a dissociation constant of $1 \times 10^{-9}$ M, an in vivo rabbit cornea penetration rate constant of $0.3\ hr^{-1}$ and is stable in solution.

All three of the above-described compounds, i.e., trifluoromethazolamide, 2-orthchlorophenylthiadiazole-5-sulfonamide and trichloromethazolamide as well as other compounds meeting the above-listed criteria are useful and operable in lowering intraocular pressure and in reducing the formation of aqueous humor by topical treatment of the eye in accordance with the invention.

Sulfonamides which are sufficiently water solubule to form a solution satisfying the above criteria may be utilized in the acid form. Those sulfonamides that are not sufficiently water soluble are utilized in the form of their pharmaceutically acceptable water soluble salts, i.e., sodium, potassium, triethanolamine, etc. The sulfonamide solutions are applied topically to the eye by exposing the entire cornea to the solution for a time sufficient for penetration into the eye of an amount of carbonic anhydrase inhibitor sufficient to effect a reduction in aqueous humor formation and intraocular pressure. The method of the invention is effective to reduce intraocular pressure at least 4 mm Hg and to reduce aqueous humor formation 30–80%. Generally, when employing solutions containing about 1–5% by weight of sulfonamide, exposure to the cornea for from about 2 to 30 minutes is adequate to enable an effective penetration of sulfonamide. The exact time of exposure will vary depending on the nature of the sulfonamide.

FIGS. 1–3 deminstrate the effect on the intraocular pressure in the eye of rabbits exposed to solutions of sulfonamides according to the invention. The shaded portions of the figures indicate the times of exposure of the eye to the active solutions. The other eye of the rabbit is used as a control. Intraocular pressure is measured utilizing the pneumotonograph according to the method of Quigley et al (Amer. J. Ophthal. Vol, 80, p. 266 (1975)). Briefly, an electronically controlled probe is gently placed on the cornea. The probe consists of a membrane, piston, and gas chamber arranged so that the eye pressure is translated electronically to a scribe on moving graph paper which records the pressure.

The volume and flow of aqueous humor is measured according to the methods of Oppelt, Invest. Ophthal., Vol. 6, p. 76 (1967).

While the invention has been described with respect to certain specific embodiments, it will be appreciated that many modifications and changes may be made by those skilled in the art without depending from the spirit of the invention. It is intended, therefore, by the appended claims to cover all such modifications and changes as fall within the true spirit and scope of the invention.

I claim:

1. The compound 2-trifluoroacetylimino-3-methyl-$\Delta^2$-1,3,4-thiadiazoline-5-sulfonamide.
2. The compound 2-trichloroacetylimino-3-methyl-$\Delta^2$-1,3,4-thiadiazoline-5-sulfonamide.

UNITED STATES PATENT AND TRADEMARK OFFICE
CERTIFICATE OF CORRECTION

PATENT NO. : 4,746,745
DATED : May 24, 1988
INVENTOR(S) : Thomas H. MAREN

It is certified that error appears in the above-identified patent and that said Letters Patent is hereby corrected as shown below:

Col. 1, following Related U.S. Patent Application Data, line 12, insert the following paragraph:

-- Research leading to the conception and reduction to practice of the invention claimed herein was supported in part by Grant No. 5-R01-02227-03 issued by the National Institutes of Health. The United States Government has certain rights in and to the claimed invention. --

Signed and Sealed this

Second Day of January, 1996

Attest:

BRUCE LEHMAN

Attesting Officer

Commissioner of Patents and Trademarks